(12) United States Patent
Kawanishi et al.

(10) Patent No.: US 7,383,082 B2
(45) Date of Patent: Jun. 3, 2008

(54) VISCERAL FAT DETERMINING DEVICE WITH A STEP-COUNTING FUNCTION

(75) Inventors: Shozo Kawanishi, Akashi (JP); Koichi Okita, Akashi (JP)

(73) Assignee: Yamato Scale Co. Ltd., Akashi-shi, Hyogo (JP)

( * ) Notice: Subject to any disclaimer, the term of this patent is extended or adjusted under 35 U.S.C. 154(b) by 349 days.

(21) Appl. No.: 10/451,580

(22) PCT Filed: Dec. 20, 2001

(86) PCT No.: PCT/JP01/11162

§ 371 (c)(1),
(2), (4) Date: Jun. 20, 2003

(87) PCT Pub. No.: WO02/051309

PCT Pub. Date: Jul. 4, 2002

(65) Prior Publication Data

US 2004/0102684 A1 May 27, 2004

(30) Foreign Application Priority Data

Dec. 22, 2000 (JP) ............................. 2000-390798

(51) Int. Cl.
*A61B 5/05* (2006.01)
(52) U.S. Cl. ....................... 600/547; 128/920
(58) Field of Classification Search ................ 235/105; 377/24.2; 600/547, 554; 702/160; 128/920; 482/8

See application file for complete search history.

(56) References Cited

U.S. PATENT DOCUMENTS

| | | | | |
|---|---|---|---|---|
| 4,220,996 A | * | 9/1980 | Searcy | 702/160 |
| 5,615,689 A | * | 4/1997 | Kotler | 600/547 |
| 6,188,925 B1 | * | 2/2001 | Kawanishi et al. | 600/547 |
| 6,322,504 B1 | * | 11/2001 | Kirshner | 600/300 |
| 6,487,445 B1 | * | 11/2002 | Serita et al. | 600/547 |
| 6,694,182 B1 | * | 2/2004 | Yamazaki et al. | 600/547 |
| 7,008,350 B1 | * | 3/2006 | Yamazaki et al. | 482/8 |

FOREIGN PATENT DOCUMENTS

| | | | |
|---|---|---|---|
| JP | 11-123182 | | 5/1999 |
| JP | 2000-166890 | * | 6/2000 |
| JP | 2000-350710 | * | 12/2000 |

OTHER PUBLICATIONS

Goran et al. Relation between visceral fat and disease risk in children and adolescents. Am J Clin Nutr. 1999; 70(suppl):149S-156S.*

(Continued)

*Primary Examiner*—Max Hindenburg
*Assistant Examiner*—Michael Apanius
(74) *Attorney, Agent, or Firm*—Alleman Hall McCoy Russell & Tuttle LLP

(57) ABSTRACT

A device is provided which is capable of determining an amount of exercise involved in walking, as well as of obtaining quantitative information about visceral fat in the abdominal part of a subject and which can be used handily by being carried with the subject. The visceral fat determining device with a step-counting function is configured as follows. The visceral fat determining device has a step-counting means for counting the number of steps involved in exercise such as walking done by a subject and a main body shaped to be portable. When body data of the subject such as the waist size of the subject is inputted to the visceral fat determining device through a manipulation section, the visceral fat determining device is capable of performing a computation of the body data based on a predetermined computing formula for obtaining quantitative information about the abdominal visceral fat of the subject.

2 Claims, 4 Drawing Sheets

OTHER PUBLICATIONS

Harris et al. Waist circumference and sagittal diameter reflect total body fat better than visceral fat in old men and women. The Health, Aging and Body Composition Study. Ann NY Acad Sci. May 2000; 904:462-473.*

Rankinen et al. The prediction of abdominal visceral fat level from body composition and anthropometry: ROC analysis. Int J Obes. 1999; 23:801-809.*

Shigeho Tanaka et al., "Aerobic Exercise Training and Life Habits as Factors Influencing Body Fat Distribution," *Bulletin of the Physical Fitness Research Institute*, No. 85, pp. 38-46, (Mar. 1994).

International Search Report, PCT/JP01/11162, Feb. 6, 2002.

Tsuji et al., "Criteria of Fatness and Diagnosis of Pathological Obesity," *Pharma Medica*, vol. 15, No. 9 (1997), pp. 13-19.

* cited by examiner

VISCERAL FAT DETERMINING DEVICE WITH A STEP-COUNTING FUNCTION

TECHNICAL FIELD

This invention relates to a visceral fat determining device with a step counting function and is capable of obtaining quantitative information about visceral fat present in an abdominal part of a human body.

BACKGROUND ART

Keeping the amount of fat in the body of a human at a proper amount is necessary in preventing adult diseases and the like to maintain human health. In keeping the amount of such body fat at a proper amount, it is necessary to keep daily energy (calorific value) intake, basal metabolism, exercise, digestion/absorption of food, and the like in balance. Exercise such as walking or running can be done in everyday life as a calorific value-consuming means. There are various instruments with which one can know the relationship between such exercise and the amount of exercise or the amount of calorific value consumed by the exercise or with which one can know the amount of fat in his or her body.

Among such instruments there is known a passometer (generally called a "pedometer"), which handily allows the user to know the amount of exercise done in walking or the amount of calorific value consumed by walking. Such a passometer is an instrument to be fitted on a waist part of a human body for counting the number of steps involved in walking or running. The passometer is capable of estimating a consumed calorific value based on a steps count and necessary personal data items such as stride, weight, and age. A passometer of another type is adapted to measure a time period taken to walk or run to find an average speed per unit time, based on what it estimates to be a consumed calorific value.

On the other hand, there is a body fat determining device as an instrument capable of determining the body fat weight or body fat ratio of a human body. The body fat determining device is adapted to determine the body fat weight or body fat ratio of a person from the bioimpedance of the person, which is the impedance of the person's body measured with electrodes brought into contact with parts of the body, and necessary personal data of the person such as the weight, height, and age of the person.

Further, there is a training device employing a cycle ergometer. This training device is adapted to provide training according to a menu which is established to include exercise corresponding to a predetermined amount of exercise or a consumed calorific value. Some of such training devices are provided at their respective handle portion with electrodes for determining the body fat ratio of a trainee.

With the aforementioned passometer, the user can know an amount of exercise or consumed calorific value based on the number of steps counted and is allowed to do exercise such as walking in accordance with a target amount of exercise or the like. However, the user cannot know a change in the fat amount in his or her body caused by the exercise measured.

Since it is believed that the so-called abdominal visceral fat, which is body fat of the type adhering to internal organs and their peripheral portions in an abdominal part of a human body, is closely correlated with adult diseases and the like, a device capable of obtaining information about such abdominal visceral fat, in particular of body fat, is needed.

The aforementioned conventional body fat determining device is capable of determining a body fat ratio or the like on a whole body basis, but is not capable of obtaining information about fat focused in the visceral part, in particular, of a human body. Thus, a device is needed which is capable of obtaining such information about fat in the visceral part of a human body. It would be desirable that such a device be of the portable type which allows an individual to carry it in everyday life, but not a large-scale instrument to be installed in a sports center or the like.

Accordingly, it is an object of the present invention to provide a device which is capable of determining the amount of exercise done in walking or like exercise while obtaining quantitative information about visceral fat in the abdominal part of a subject and which can be used handily as carried with the subject every day.

SUMMARY OF THE INVENTION

A visceral fat determining device with a step-counting function according to the present invention is configured such that:

the visceral fat determining device has step-counting means for counting the number of steps involved in exercise such as walking done by a subject, and a main body shaped to be portable;

the visceral fat determining device allows entry of body data of the subject including the waist size of the subject, which is the circumferential size of a trunk part of the subject;

the visceral fat determining device is capable of obtaining quantitative information about abdominal visceral fat of the subject through a computation of the body data based on a predetermined computing formula;

the visceral fat determining device has display means for displaying results of determinations obtained;

the computation based on the computing formula for obtaining the quantitative information about abdominal visceral fat of the subject is performed using data including the waist size of the subject; and the display means is capable of displaying at least the number of steps counted by the step-counting means.

The visceral fat determining device with a step-counting function thus configured according to the present invention is capable of determining the amount of exercise involved in exercise such as walking represented through step-count data as well as of obtaining quantitative information about the abdominal visceral fat of a subject based on the waist size of the subject. Since the visceral fat determining device with a step-counting function according to the present invention is shaped to be portable so that the subject can carry it every day, the visceral fat determining device is capable of determining the amount of exercise involved in exercise such as walking and readily obtaining quantitative information about the abdominal visceral fat of the subject at any time. If the abdominal visceral fat is measured before and after walking, the subject can know quantitative information about a change in visceral fat caused by exercise such as walking readily at any time.

A visceral fat determining device with a step-counting function according to the present invention may be configured such that:

the visceral fat determining device has step-counting means for counting the number of steps involved in exercise such as walking done by a subject, and a main body shaped to be portable;

the visceral fat determining device allows entry of body data of the subject including the waist size of the subject, which is the circumferential size of a trunk part of the subject;

the visceral fat determining device is capable of determining an abdominal visceral fat cross-sectional area of the subject through a computation of the body data based on a predetermined computing formula;

the visceral fat determining device has display means for displaying results of determinations obtained;

the computation based on the computing formula for determining the abdominal visceral fat cross-sectional area of the subject is performed using data including the waist size of the subject as the body data; and the display means is capable of displaying at least the number of steps counted by the step-counting means.

The visceral fat determining device with a step-counting function thus configured according to the present invention is capable of determining the amount of exercise involved in exercise such as walking, represented through step-count data, as well as of determining an abdominal visceral fat cross-sectional area, which is closely correlated with the amount of visceral fat as quantitative information about the abdominal visceral fat of a subject based on the waist size of the subject.

Since the visceral fat determining device with a step-counting function according to this configuration of the present invention is shaped to be portable so that the subject can carry it every day, the visceral fat determining device is capable of determining the amount of exercise involved in exercise such as walking and the abdominal visceral fat cross-sectional area of the subject readily at any time. If the abdominal visceral fat cross-sectional area of the subject is determined before and after walking, the subject can know quantitative information about a change in the visceral fat caused by exercise such as walking readily at any time.

A visceral fat determining device with a step-counting function may be configured such that:

the visceral fat determining device is capable of storing step-count data obtained by the step-counting means; and the visceral fat determining device has visceral fat change computing means for performing a computation to find a change in abdominal visceral fat cross-sectional area relative to the step-count data based on a first abdominal visceral fat cross-sectional area determined through a computation based on first body data, step-count data obtained by the step-counting means after the first abdominal visceral fat cross-sectional area is determined, and a second abdominal visceral fat cross-sectional area determined thereafter through a computation based on second body data.

The visceral fat determining device with a step-counting function thus configured according to the present invention is capable of computing and estimating a change in the abdominal visceral fat cross-sectional area determined from the first and second abdominal visceral fat cross-sectional areas determined before and after exercise, such as walking, as a change relative to the amount of exercise represented by the step-count data obtained by the step-counting means. This allows a subject to appreciate more clearly the effect of exercise such as walking in consuming abdominal visceral fat.

The computation for determining a change in abdominal visceral fat relative to step-count data may include finding a difference in the abdominal visceral fat cross-sectional area, which is the difference between the first abdominal visceral fat cross-sectional area and the second abdominal visceral fat cross-sectional area, and finding the ratio of the difference in abdominal visceral fat cross-sectional area to the step-count data. Otherwise, the computation may include determining the amount of exercise such as a walking distance from step-count data and finding the ratio of the difference in the abdominal visceral fat cross-sectional area to the amount of exercise. Still otherwise, the computation may include determining a visceral fat amount corresponding to the difference in abdominal visceral fat cross-sectional area and finding the ratio of the visceral fat amount to a consumed calorific value determined from the step-count data. Such computations for determining a change in abdominal visceral fat relative to step-count data include various computations for evaluating the change in abdominal visceral fat relative to the amount of exercise determined based on the step-count data by determining a change in abdominal visceral fat cross-sectional area before and after exercise such as walking from the difference between the first abdominal visceral fat cross-sectional area and the second abdominal visceral fat cross-sectional area.

The visceral fat determining device with a step-counting function may comprise:

visceral fat determination instruction instructing means for instructing the determination of the first abdominal visceral fat cross-sectional area through the computation based on the first body data and the determination of the second abdominal visceral fat cross-sectional area through the computation based on the second body data; and step counting start instructing means for instructing the start of counting of step-count data when the termination of the computation for determining the first abdominal visceral fat is detected, wherein:

when the termination of the step counting by the step-counting means is detected, the visceral fat determination instructing means instructs the determination of the second abdominal visceral fat cross-sectional area; and the visceral fat change computing means performs computation for determining the change in abdominal visceral fat relative to the step-count data based on the first and second abdominal visceral fat cross-sectional areas determined and the step-count data.

With this configuration, it is possible to achieve the determination of the first abdominal visceral fat cross-sectional area before the start of exercise such as walking, the counting of step-count data of exercise such as walking and the determination of the second abdominal visceral fat cross-sectional area after the exercise reliably without any operation error or the like and, hence, the determination of a change in abdominal visceral fat cross-sectional area relative to exercise such as walking can be made reliable.

The visceral fat change computing means may be configured to perform a computation based on the step-count data to find a calorific value consumed by exercise such as walking done by the subject as well as to find a visceral fat consumption ratio, which is a change in abdominal visceral fat relative to the consumed calorific value as the change in abdominal visceral fat relative to the step-count data. This configuration is adapted to find a consumed calorific value as an amount of exercise corresponding to the number of steps based on the step-count data and, hence, the subject can appreciate a change in abdominal visceral fat relative to a consumed calorific value represented as an amount of energy. This configuration is convenient because a change in abdominal visceral fat can be made to clearly correspond to intake of food or the like through the consumed calorific value.

The visceral fat determining device with a step-counting function, which is capable of determining a consumed calorific value and a visceral fat consumption ratio as a result of exercise such as walking done by the subject, may be configured to allow entry of the stride and weight of the subject, wherein the visceral fat change computing means is capable of finding the consumed calorific value and the visceral fat consumption ratio based on the step-count data obtained and the stride and weight entered of the subject.

This configuration is capable of determining a consumed calorific value, which is an amount of energy consumed by exercise such as walking done by the subject over a fixed distance, from the step-count data and the stride and weight data entered of the subject. The visceral fat consumption ratio can be found from the consumed calorific value thus determined and the change in abdominal visceral fat.

The visceral fat determining device with a step-counting function, which is capable of determining a consumed calorific value and a visceral fat consumption ratio as results of exercise such as walking done by the subject, may be configured to be capable of storing the visceral fat consumption ratio as well as of performing a computation to estimate the consumed calorific value from the visceral fat consumption ratio and the amount of the change in abdominal visceral fat found from the first and second abdominal visceral fat cross-sectional areas determined.

Alternatively, the visceral fat determining device with a step-counting function, which is capable of determining a consumed calorific value and a visceral fat consumption ratio as a result of exercise such as walking done by the subject, may be configured to be capable of storing the visceral fat consumption ratio as well as of performing a computation to estimate the amount of the change in abdominal visceral fat from the visceral fat consumption ratio and the consumed calorific value determined based on the step-count data determined.

The visceral fat consumption ratio to be determined is a rate of consumed abdominal visceral fat per a fixed amount of exercise converted to a consumed calorific value and is inherent to the constitution of an individual subject. Once the abdominal visceral fat consumption ratio is determined, determination of a calorific value consumed by exercise allows estimation of the amount of consumed abdominal visceral fat from the consumed calorific value thus determined and the abdominal visceral fat consumption ratio. Alternatively, if a change in abdominal visceral fat as a result of consumption of abdominal visceral fat is determined, it is possible to estimate a consumed calorific value from the change in abdominal visceral fat thus determined and the visceral fat consumption ratio.

The visceral fat determining device with a step-counting function, which is capable of determining a consumed calorific value and a visceral fat consumption ratio as results of exercise such as walking done by the subject, may be configured to be capable of storing the consumed calorific value and the visceral fat consumption ratio; and the visceral fat change computing means is capable of finding a steps count, a walking distance and a consumed calorific value which are needed to consume a given target amount of visceral fat based on the step-count data, the consumed calorific value stored and the visceral fat consumption ratio stored.

With this configuration the subject can know a steps count, a walking distance, and a consumed calorific value, which are needed to consume a given amount of abdominal visceral fat established as a target value if the subject wants to consume the given amount of abdominal visceral fat. This configuration is convenient because such a steps count or the like can serve as a measure of exercise such as walking.

The visceral fat determining device with a step-counting function, which is capable of storing the stride and weight of the subject, may be configured to be capable of measuring a time period elapsed after starting of step counting by the step-counting means, wherein the visceral fat change computing means is configured to determine a distance the subject travels from the step-count data and the stride, and an average traveling speed from the distance of the travel and the time period taken by the travel as well as to determine a calorific value consumed by the travel based on the average traveling speed.

The visceral fat determining device with a step-counting function, which is capable of determining the visceral fat consumption ratio, may be configured to be capable of:

measuring a time period elapsed after starting of step counting by the step-counting means and determining abdominal visceral fat cross-sectional areas at predetermined time intervals after starting of a specific kind of exercise such as walking;

comparing the abdominal visceral fat cross-sectional areas determined at the predetermined time intervals with the first abdominal visceral fat cross-sectional area sequentially and measuring a time period until a difference between the first abdominal visceral fat cross-sectional area and any one of the abdominal visceral fat cross-sectional areas determined at the predetermined time intervals is detected, thereby measuring a time period from the start of the specific kind of exercise until combustion of visceral fat starts;

storing a visceral fat combustion starting time period which is a time period elapsed until the start of the visceral fat combustion; and performing a computation to find a consumed calorific value consumed by exercise such as walking done by the subject based on step-count data obtained by the step-counting means after lapse of the visceral fat consumption starting time period from the start of the specific kind of exercise and determining a corrected visceral fat consumption ratio as a change in abdominal visceral fat relative to the consumed calorific value thus found.

With this visceral fat determining device with a step-counting function it is possible to determine a visceral fat consumption ratio relative to a consumed calorific value consumed by exercise such as walking done by the subject based on the step-count data obtained after the start of consumption of the abdominal visceral fat itself, or after lapse of the visceral fat consumption starting time period.

Consumption of the abdominal visceral fat of a human body starts not just after the start of exercise such as walking, but also after lapse of a certain time period from the start of consumption of glycogen and the like stored in the human body. Accordingly, if one wants to know a steps count, a consumed calorific value or the like corresponding to a direct consumption of the abdominal visceral fat itself, it is necessary to know a steps count, a consumed calorific value or the like after the start of consumption of the abdominal visceral fat itself according to the consumption mechanism of a human body. The certain time period up to the start of consumption of the abdominal visceral fat itself is an inherent one that is dependent on the kind of exercise such as walking, running, or the like and the constitution or the like of a subject.

The visceral fat determining device with a step-counting function of this configuration is capable of measuring such a certain time period as the fat combustion starting time period. After the fat combustion starting period is measured, the visceral fat determining device determines a corrected visceral fat consumption ratio as a change in abdominal visceral fat relative to a consumed calorific value consumed after lapse of the visceral fat consumption starting time period. From such a corrected visceral fat consumption ratio, one can know the change in abdominal visceral fat relative to the consumed calorific value connected with direct consumption of the abdominal visceral fat itself.

The visceral fat determining device with a step-counting function, which is capable of determining the visceral fat consumption ratio, may be configured to find the average value of visceral fat consumption ratios as a result of the determination being performed a plurality of times, or to find the cumulative sum of the visceral fat consumption ratios as a result of the determination being performed plurality times.

Alternatively, the visceral fat determining device with a step-counting function, which is capable of determining the corrected visceral fat consumption ratio, may be configured to find the average value of corrected visceral fat consumption ratios as a result of the determination being performed a plurality of times, or to find the cumulative sum of the corrected visceral fat consumption ratios as a result of the determination being performed a plurality of times.

The visceral fat determining device with a step-counting function, which is capable of determining the abdominal visceral fat cross-sectional area of the subject, may be configured such that:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject.

The visceral fat determining device with a step-counting function, which is capable of determining the abdominal visceral fat cross-sectional area of the subject, may be configured to allow entry of body data of the subject including the waist size, height, and weight of the subject, the waist size being the circumferential size of a trunk part of the subject, wherein:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject and a BMI found from the height and weight of the subject.

The visceral fat determining device with a step-counting function, which is capable of determining the abdominal visceral fat cross-sectional area of the subject, may be configured to allow entry of body data of the subject including the waist size, height, weight, and abdominal subcutaneous fat thickness of the subject, the waist size being the circumferential size of a trunk part of the subject, wherein:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject, a BMI found from the height and weight of the subject and the abdominal subcutaneous fat thickness.

The visceral fat determining device with a step-counting function, which is capable of determining the abdominal visceral fat cross-sectional area of the subject, may have body fat ratio measurement means capable of determining the body fat ratio of the subject based on the impedance of the body of the subject that is measured via electrodes brought into contact with terminals on the body of the subject, wherein:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size and body fat ratio of the subject.

The visceral fat determining device with a step-counting function, which is capable of determining the abdominal visceral fat cross-sectional area of the subject, may be configured to allow entry of body data of the subject including the waist size and abdominal subcutaneous fat thickness of the subject, the waist size being the circumferential size of a trunk part of the subject, and to have body fat ratio measurement means capable of determining the body fat ratio of the subject based on the impedance of the body of the subject that is measured via electrodes brought into contact with terminals of the body of the subject, wherein:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size, abdominal subcutaneous fat thickness, and body fat ratio of the subject.

The visceral fat determining device with a step-counting function, which is capable of determining the abdominal visceral fat cross-sectional area of the subject, may be configured to allow entry of body data of the subject including the waist size, height, and weight of the subject, the waist size being the circumferential size of a trunk part of the subject, and to have body fat ratio measurement means capable of determining the body fat ratio of the subject based on the impedance of the body of the subject that is measured via electrodes brought into contact with terminals on the body of the subject, wherein:

the computing formula for determining the abdominal visceral fat cross-sectional area is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject, a BMI found from the height and weight of the subject, and the body fat ratio of the subject.

The visceral fat determining device with a step-counting function, which is capable of determining the abdominal visceral fat cross-sectional area of the subject, may be configured to allow entry of body data of the subject including the waist size, height, weight, and abdominal subcutaneous fat thickness of the subject, the waist size being the circumferential size of a trunk part of the subject, and have body fat ratio measurement means capable of determining the body fat ratio of the subject based on the impedance of the body of the subject that is measured via electrodes brought into contact with terminals of the body of the subject, wherein:

the computing formula for determining the abdominal visceral fat cross-sectional area is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject, a BMI found from the height and weight of the subject, and the abdominal subcutaneous fat thickness and body fat ratio of the subject.

The visceral fat determining device with a step-counting function, which is capable of determining the abdominal visceral fat cross-sectional area of the subject, may have impedance measurement means capable of measuring the impedance of the body of the subject via electrodes brought into contact with terminals on the body of the subject, wherein:

the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject and the impedance of the body of the subject.

The visceral fat determining device with a step-counting function, wherein the computing formula for finding the abdominal visceral fat cross-sectional area is created by statistical processing of correlations between actual visceral fat cross-sectional areas of a large number of human bodies as samples that are measured by tomography of the abdominal parts of the human bodies and body data of the human bodies as the samples, may be configured such that the computation based on the computing formula for determining the abdominal visceral fat cross-sectional area is performed using a correction term based on the age of the subject and/or a correction term based on the sex of the subject.

DETAILED DESCRIPTION AND BEST MODE FOR CARRYING OUT THE INVENTION

Figure 1:
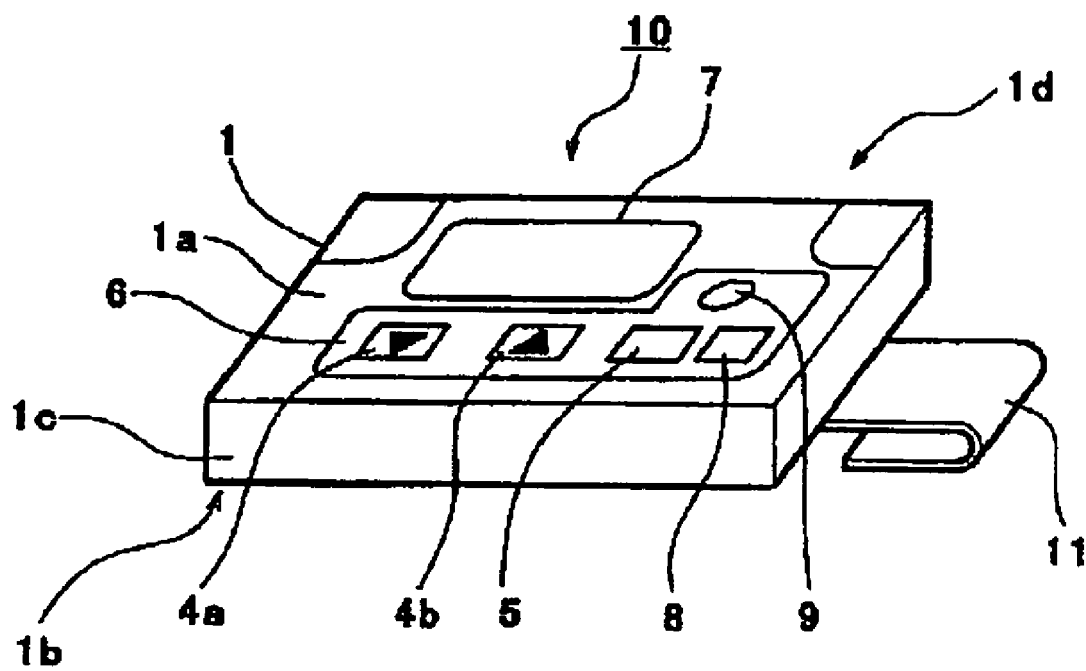
FIG. 1 is a perspective view showing a visceral fat determining device with a step-counting function.

The best mode for carrying out the present invention will be described with reference to FIGS. 1 to 4. FIG. 1 is a perspective view showing a visceral fat determining device with a step-counting function 10 (hereinafter referred to as "visceral fat determining device 10") as one embodiment of the present invention. As will be described in detail, the visceral fat determining device 10 is configured to be capable of determinations in relation to visceral fat in the abdominal part of a subject as well as to have a function as an instrument generally called "passometer."

That is, the visceral fat determining device 10 is of a construction in which members for performing determinations in relation to abdominal visceral fat and step-counting means functioning as a passometer are integrally incorporated in a main body 1.

The visceral fat determining device 10 can be carried by a person in everyday life if the main body 1 is attached to a belt trained around the waist portion of clothing of the person by means of a fitting 11. The main body 1 has a weight and size such as to allow the person to carry the visceral fat determining device 10 for everyday use.

The visceral fat determining device 10 may be fitted to a human body by attaching the main body 1 to a hat, a necklace, or a pocket or by winding it around a wrist like a watch, or in other various manners of fitting for allowing the visceral fat determining device 10 to be carried on the human body.

The main body 1 is shaped into a card having an obverse side 1a, a reverse side 1b and four peripheral sides therearound including a front side 1c and a rear side 1d. The obverse side 1a of the main body 1 is provided with a manipulation section 6 and a display section 7. In the manipulation section 6 there are provided a switch key 8, a start/stop key 9 and data entry keys including a select key 5 and a decrement key 4a as manipulation keys.

The switch key 8 is a key for selecting any one of plural functions of the visceral fat determining device 10. Specifically, manipulating the switch key 8 allows selection of use of the visceral fat determining device 10 as a passometer or in a determination relating to visceral fat, or both in combination.

When a mode that combines determinations relating to visceral fat and step-counting is selected through manipulation of the switch key 8, a visceral fat change computation control routine to be described later becomes ready to be executed. The start/stop key 9 is a key for starting or terminating the step counting by step-counting means to be described later.

The data entry keys are keys for inputting body data of a subject, including the waist size, weight, and the like of the subject, to the visceral fat determining device 10. The visceral fat determining device 10 is provided with select key 5 for selecting body data items, decrement key 4a for decreasing numeric data, and increment key 4b for increasing numeric data.

Entry of various data comprising numeric data is possible through manipulation of the keys 4a and 5 and like keys. Such data entry keys may consist of a so-called "numeric keypad."

Keys 4a, 4b, and 5 allow entry of necessary body data in accordance with the aforementioned functions selected through manipulation of the switch key 8. Specifically, when the function of visceral fat determinations, for example, is selected through manipulation of the switch key 8, the items that can be selected through the select key 5 are body data items to be needed in visceral fat determinations. Alternatively, when use of the visceral fat determining device 10 as a passometer is selected, the items that can be selected through the select key 5 are body data items that allow the visceral fat determining device 10 to function as a passometer.

The body data items that allow the visceral fat determining device 10 to function as a passometer include weight, stride, and unit-consumed calorific value. On the other hand, the body data items that are needed in visceral fat determinations include waist size, height, weight, abdominal subcutaneous fat thickness, sex, and age. The term "waist size," as used herein, means the circumferential size of a trunk part of the body of a subject.

Desirably, the circumferential size of a trunk part at or around the fourth lumbar vertebra of a human body is used as the waist size. This is because the circumferential size of such a part as the waist size is considered to reflect best the condition of obesity and the like of the upper part of the body of a subject.

The term "abdominal subcutaneous fat thickness" is the thickness of subcutaneous fat in the abdominal part. The abdominal subcutaneous fat thickness may be one measured by any well known subcutaneous fat thickness measurement means such as a so-called caliper or means using ultrasonic wave.

Such an abdominal subcutaneous fat thickness may be collected from a body part adjacent the navel of a human body or a body part above the ilium of the human body. It is possible to employ one of the measured values collected from these two body parts or the mean value of the measured values as the abdominal subcutaneous thickness.

The display section 7 is adapted to display various body data items inputted through manipulation of the aforementioned manipulation keys and the results of determinations in relation to visceral fat or of step counting performed when the visceral fat determining device 10 is used as a passometer. The display section 7 further displays an indication of the starting of each determination accompanying the execution of the visceral fat change computation control routine to be described later, as well as a visceral fat consumption ratio and the like found through the execution of the visceral fat change computation control routine. Furthermore, the display section 7 is capable of representing the results of determinations in relation to visceral fat or of the step counting as graphs.

The visceral fat determining device 10 incorporates therein step-counting means not particularly shown for the visceral fat determining device 10 to function as a passometer. The step-counting means may comprise various well-known devices capable of detecting up-and-down movement of a human body involved in human walking or running of the human. For example, the step-counting means may comprise a combination of a magnet, a spring and a sensor, a piezo-electric transducer, an electromagnetic pickup, a Hall effect element, or other arrangement adapted to detect up-and-down movement of a human body with use of an accelerometer and summate up-and-down movements thus detected thereby counting steps. The visceral fat determining device 10 is provided therein with a clock for measuring a time period elapsed after the starting of step counting.

Figure 2:
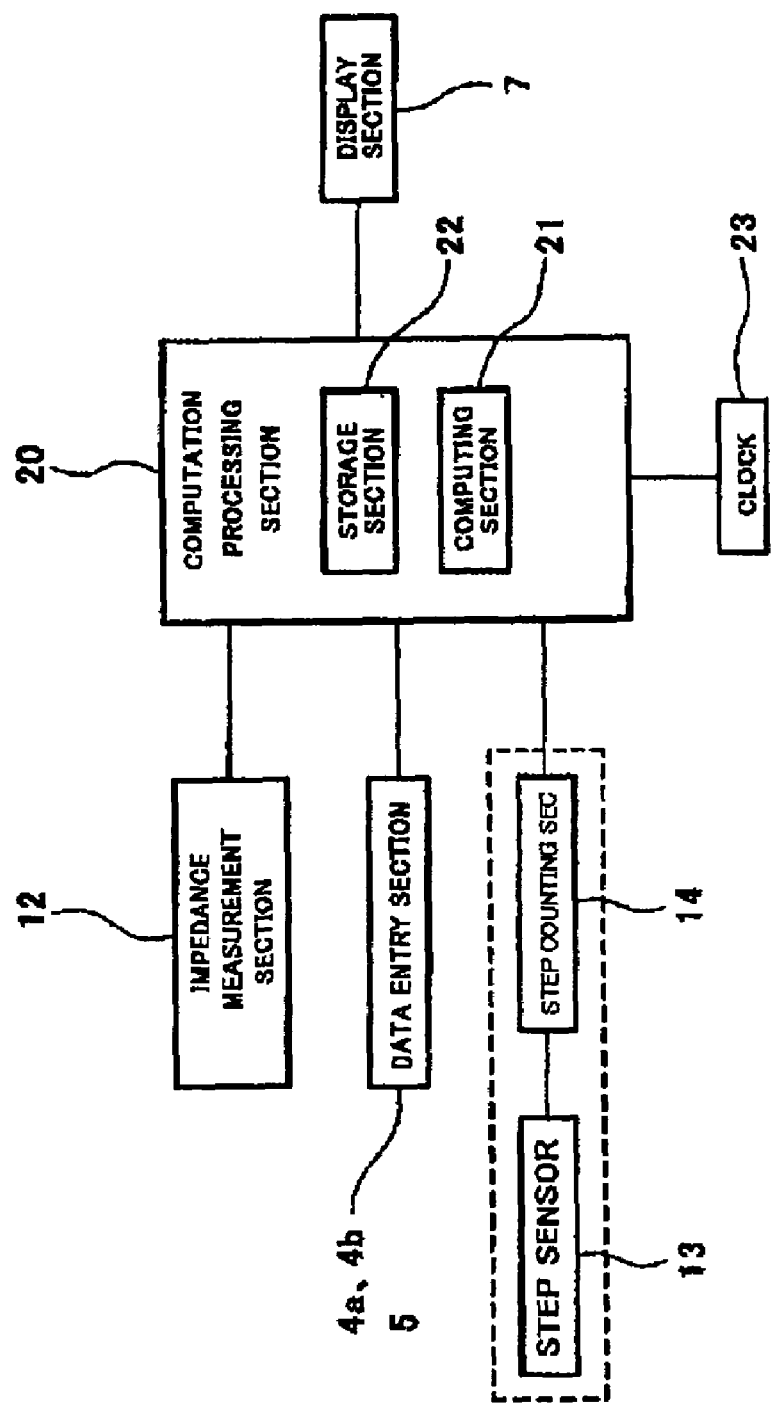
FIG. 2 is a block diagram of the visceral fat determining device with a step-counting function.

Next, description will be made of blocks associated with the signal processing of the visceral fat determining device 10 with reference to FIG. 2. The visceral fat determining device 10 has a computation processing section 20 for performing various computations, the computation processing section 20 comprising a computing section 21 and a storage section 22. Specifically, the computation processing section 20 performs computations related to visceral fat determinations based on various body data items, computations for finding an amount of exercise involved in walking, running, or the like, type of exercise, and a consumed calorific value consumed by such exercise, and computations in relation to a change in abdominal visceral fat relative to the amount of exercise or the consumed calorific value.

The storage section 22 is adapted to store body data of a subject such as the waist size, weight, and height of the subject inputted through manipulation of, for example, the manipulation key 4a of the data entry section. The storage section 22 is adapted to further store the number of steps counted by the step-counting means comprising a step sensor 13 and a step-counting section 14, as well as a time period measured by the clock 23.

The storage section 22 also stores a computing formula for finding the BMI of a subject and, hence, the visceral fat determining device 10 is capable of finding the BMI. A BMI can be found relatively easily as an indicator of obesity from the formula: $(weight)/(height)^2$. Once the BMI is found, it is subjected to data processing as one body data item characteristic of the body of the subject.

The storage section 22 also stores computing formulae to be used for estimation of the abdominal visceral fat cross-sectional area of the subject as quantitative information about the abdominal visceral fat of the subject through a computation based on various body data items. The following formulae (1) to (3) are stored as such computing formulae to be used for estimation of the abdominal visceral fat cross-sectional area of the subject through a computation.

$$VA = a_1 \cdot W_L + c_1 \tag{1}$$

$$VA = a_2 \cdot W_L + b_1 \cdot BMI + c_2 \tag{2}$$

$$VA = a_4 \cdot W_L + b_2 \cdot BMI + e_1 \cdot s + c_4 \tag{3}$$

In the formulae (1) to (3), VA represents an abdominal visceral fat cross-sectional area, $W_L$ represents a waist size, and s represents an abdominal subcutaneous fat thickness.

In the formulae (1) to (3), $a_1$, $a_2$, $a_4$, $b_1$, $b_2$, $c_1$, $c_2$, $c_4$, and $e_1$ are coefficients obtained in the processes of creating these formulae according to methods to be described later.

The abdominal visceral fat cross-sectional area (VA) found through a computation based on any one of the formulae (1) to (3) is the cross-sectional area of fat present in the visceral part in the abdominal cavity of a human body. More specifically, the abdominal visceral fat cross-sectional area (VA) is the cross-sectional area of a fat portion adhering to internal organs and their periphery cut along any cross section between a cross section cut through the position of the first lumbar vertebra of a human body in an erected position or through a point adjacent thereto and a cross-section cut through the position of the fifth lumbar vertebra of the human body in the erected position or through a point adjacent thereto.

In finding such an abdominal visceral fat cross-sectional area, it is particularly desirable to find the visceral fat cross-sectional area along a cross-section cut through the position of a middle portion of the fourth lumbar vertebra. This is because the visceral fat cross-sectional area along such a cross-section is considered to highly correlate with the amount of visceral fat in the abdominal part of a human body.

The formulae (1) to (3) are created in the following manner separately.

That is, the actual abdominal visceral fat cross-sectional area of each individual of an unspecified number of human bodies serving as samples and various items of body data to be used in the formulae (1) to (3) noted above is determined. Subsequently, assumption is made that the body data items to be used in each computing formula and the actual abdominal visceral fat cross-sectional area have correlations with each other, which are then statistically processed to create each of the formulae (1) to (3).

Referring to the creation of the formulae (1) to (3) more specifically, assumption is made that the actual abdominal visceral fat cross-sectional area determined of each individual of the samples has correlations with the waist size of that individual with each other, and the correlations are statistically processed to create the formula (1). In the formula (1), the coefficient $a_1$ with respect to $W_L$ is the first regression coefficient of waist size, and the coefficient $c_1$ is a first regression coefficient.

With respect to formula (2), assumption is made that the actual abdominal visceral fat cross-sectional area determined of each individual of the samples has correlations with the waist size and BMI of that individual, and the correlations are statistically processed to create the formula (2). In the formula (2), the coefficient $a_2$ with respect to $W_L$ is the second regression coefficient of waist size, the coefficient $b_1$ with respect to BMI is the first regression coefficient of BMI, and the coefficient $c_2$ is a second regression coefficient.

With respect to formula (3), assumption is made that the actual abdominal visceral fat cross-sectional area determined of each individual of the samples has correlations with the waist size, BMI and abdominal subcutaneous fat thickness of that individual, and the correlations are statistically processed to create the formula (3). In the formula (3), the coefficient $a_4$ with respect to $W_L$ is the fourth regression coefficient of waist size, the coefficient $b_2$ with respect to BMI is the second regression coefficient of BMI, the coefficient $e_1$ with respect to s is the first regression coefficient of abdominal subcutaneous fat thickness, and the coefficient $c_4$ is a fourth regression coefficient.

The determination of the abdominal visceral fat cross-sectional area of a human body serving as a sample can be achieved by tomography. The part of a human body at which the abdominal visceral fat cross-sectional area of the human body is to be determined is selected so as to correspond to the body part at which the VA is to be determined by the visceral fat determining device 10. As described above, it is particularly desirable to select a cross-section cut through the position of a middle portion of the fourth lumbar vertebra.

It is possible to use various tomographic methods that are capable of accurately measuring a cross section of the abdominal part of a human body such as CT-scan, MRI, and ultrasonic diagnostics as methods to be employed in determination of the abdominal visceral fat cross-sectional area of a human body as a sample.

In creating the formulae (2) and (3) the statistical processing of the correlations between two or more body data items and an abdominal visceral fat cross-sectional area can be achieved by multiple linear regression analysis.

In creating the formulae (1) to (3) the number of human bodies serving as samples for collecting abdominal visceral fat cross-sectional areas and body data is desirably 100 or more in view of statistical processing of abdominal visceral fat cross-sectional areas. More desirably, the number of human bodies is 500 or more.

With the formula (1) it is possible to determine the VA of a subject which reflects the waist size of the subject because computation is performed using data including the waist size of the subject as body data of the subject.

With the formula (2) it is possible to determine the VA of a subject which reflects the waist size and BMI of the subject because computation is performed using data including the waist size and BMI of the subject as body data of the subject.

With the formula (3) it is possible to determine the VA of a subject which reflects the waist size, BMI and abdominal subcutaneous fat thickness of the subject because computation is performed using data including the waist size, BMI, and abdominal subcutaneous fat thickness of the subject as body data of the subject.

Of the formulae (1) to (3) noted above one for determining the VA of a subject from a larger number of body data items is capable of determining the VA more accurately because it allows the body condition of the subject to be reflected more precisely from more different angles.

It is possible to add a correction term based on the age of a subject or a correction term based on the sex of the subject to each of the formulae (1) to (3). Correction term Yc based on the age of the subject and correction term Xc based on the sex of the subject are represented by the following formulae (4) and (5), respectively.

$$Yc = -\delta \cdot age \qquad (4)$$

$$Xc = \eta \cdot sex \qquad (5)$$

In the formula (4), age is the age of a subject, and $\delta$ is an age correction coefficient. In the formula (5), sex is a variable which varies according to whether the subject is a man or a woman, and $\eta$ is a sex correction coefficient. If these correction terms are added to each of the formulae (1) and (3), they are defined and used as variable terms of a multiple linear regression formula. Accordingly, $\delta$ and age in the formula (4) can be found as a regression variable and a variable, respectively, based on their correlations with an estimate equation for estimating VA, while $\eta$ and sex in the formula (5) can be found as a regression coefficient and a variable, respectively, based on their correlations with an estimate equation for estimating VA.

If the correction term Yc of the formula (4) or the correction term Xc of the formula (5) is added to each of the formulae (1) to (3) to determine VA, the VA thus determined reflects personal characteristics of the subject more precisely based on the age or sex of the subject.

It is possible to add either or both of the correction terms Xc and Yc to each of the formulae (1) to (3). If the correction terms Xc and Yc are both added to each of the formulae (1) to (3) to determine VA, the VA thus determined reflects personal characteristics of the subject much more precisely.

The storage section 22 stores the visceral fat change computation control routine. When the visceral fat change computation control routine is executed, the visceral fat determining device 10 gives the user an indication of abdominal visceral fat determination and an indication of the start of step counting while performing a computation to find the amount of a change in visceral fat with consumption of visceral fat caused by exercise such as walking.

Next, description will be made of an exemplary operation of the visceral fat determining device 10 by way of an example of usage that allows the user to know the amount of a change in abdominal visceral fat caused by walking or like exercise. When the switch key 8 is manipulated, a determination mode is selected in which a combined function of visceral fat determination and step counting can be executed. This causes the visceral fat change computation control routine shown in FIG. 3 to be executed.

First, necessary items of body data of a subject such as the height, weight, age, sex, and stride of the subject are inputted to the visceral fat determining device 10 (step S1). In the case where a computation based on the formula (3) is performed to determine the abdominal visceral fat cross-sectional area of the subject at later step S4, the abdominal subcutaneous fat thickness of the subject is also inputted to the visceral fat determining device 10.

Subsequently, the starting of determination related to the visceral fat of the subject is instructed (step S2). According to this indication (step S2, Y), the waist size of the subject is inputted (step S3).

In turn, a first abdominal visceral fat cross-sectional area (VA1) is determined through a computation based on the waist size inputted at step S3 (step S4). The computation for determining the first abdominal visceral fat cross-sectional area VA1 at step S4 is based on the formulae (1) to (5). The first abdominal visceral fat cross-sectional area VA1 thus determined is stored and can be displayed at the display section 7.

Then, an indication to inquire whether visceral fat determination is to be terminated or not is given (step S5). If the visceral fat determination is to be terminated (step S5, Y), an indication is given to inquire whether step counting is to be started or not (step S6). According to the indication (step S6, Y), the subject manipulates the start/stop key 9 to make the step-counting means ready to count steps. Thus, steps involved in walking or like exercise done by the subject are counted (step S7).

Subsequently, an indication is given to inquire whether the counting of steps is to be stopped or not (step S8). When the subject manipulates the start/stop key 9 to stop the step counting (step 8, Y), the step counting is stopped (step S9). The number of steps thus counted is stored as step-count data and can be displayed at the display section 7 (step S10). In addition, a computation is performed to find a consumed calorific value (K) that has been consumed from the body of the subject by the exercise involving such a steps count. The consumed calorific value thus found is stored and can be displayed at the display section 7 (step S10). The consumed calorific value found at step S10 is the product of a steps count X a stride X a weight X a unit consumed calorific value (a calorific value consumed per unit weight and unit walking distance).

In turn, the starting of determination related to the visceral fat of the subject is instructed again (step S11). According to this indication (step S11, Y), the waist size of the subject is inputted (step S12).

Subsequently, a second abdominal visceral fat cross-sectional area (VA2) is determined through a computation based on the waist size inputted at step S12 (step S13). The computation for determining the second abdominal visceral fat cross-sectional area VA2 at step S13 is performed using the same one of the formulae (1) to (5) as used to determine the first abdominal visceral fat cross-sectional area VA1 at step S4. The second abdominal visceral fat cross-sectional area VA2 thus determined is stored and can be displayed at the display section 7.

In turn, the amount of a change in abdominal visceral fat (ΔVA) caused by exercise such as walking is computed based on the first and second abdominal visceral fat cross-sectional areas VA1 and VA2 (step S14). The amount of the change in abdominal visceral fat can be stored and displayed at the display section 7. A computation is then performed to find a fat consumption ratio (ΔVA/K) based on the amount of the change in abdominal visceral fat (ΔVA) and the consumed calorific value (K) (step S15). The fat consumption ratio thus found is stored and can be displayed at the display section 7 (step S15).

The foregoing description has been made of the operation for determining the relationship between a consumed calorific value determined based on step-count data and the amount of a change in abdominal visceral fat as an exemplary operation for determining a change in abdominal visceral fat before and after exercise. Besides this operation, it is possible to perform operations for obtaining various data representing the relationship between step-count data and a change in abdominal visceral fat. For example, it is possible to perform an operation for determining a step count itself and a change in abdominal visceral fat before and after exercise. This operation also allows the user to know how much change in abdominal visceral fat is caused by a fixed steps count.

Alternatively, it is possible to perform an operation for determining the relationship between a steps count and an abdominal visceral fat amount determined through an approximating computation based on an abdominal visceral fat cross-sectional area. After all, any operation is possible as long as it can determine the relationship between an amount of exercise based on and reflected by step-count data and any quantitative change in abdominal visceral fat.

Figure 3:
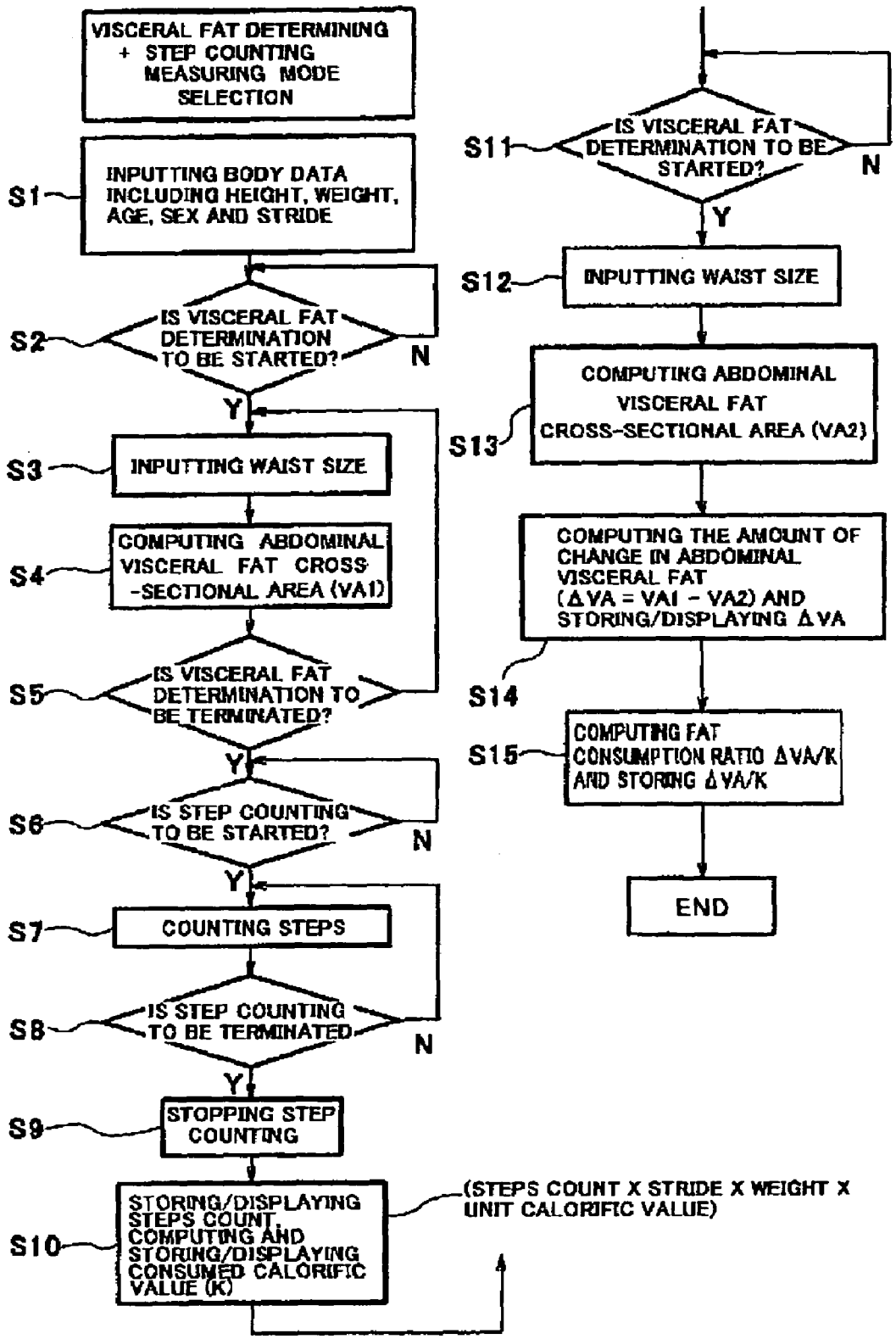
FIG. 3 is a flow chart of a visceral fat change computation control routine.

The visceral fat determining device 10 is also capable of determining a consumed calorific value consumed in the body of a subject from a walking speed (or running speed), which is a traveling speed of the subject. If the procedure from step S6 to step S10 in the visceral fat change computation control routine shown in FIG. 3 is replaced with the procedure from step S16 to step S25 shown in FIG. 4, it is possible to determine a consumed calorific value consumed in the body of the subject from a walking speed of the subject. Specifically, an indication is given to inquire whether step counting is to be started or not (step S16), and then according to this indication (step S16, Y) the subject manipulates the start/stop key 9 is make the passometer ready to count steps. Subsequently, counting of walking time is started (step S17), and the number of steps is counted (step S18).

In turn, an indication is given to inquire whether the step counting is to be terminated or not (step S19). When the subject manipulates the start/stop key 9 to stop the step counting (step 19, Y), the step counting is terminated (step S20). The number of steps thus counted is stored as step-count data and can be displayed at the display section 7 (step S20). The counting of time is also stopped (step S21). The time thus counted, which is a walking time period taken for the subject to travel a walking distance to be determined later, is stored and can be displayed at the display section 7 (step S21).

In turn, the walking distance, which is the distance the subject has traveled, is determined (step S22). The walking distance is computed as the product of a steps count by a stride. The average walking speed, which is the average traveling speed, is computed from the walking distance determined at step S22 and the walking time period determined at step S21 (step S23). Subsequently, the amount of consumed energy (unit calorific value (Kcal/Kg/min) is determined (step S24). The consumed calorific value is then determined (step S25). The consumed calorific value thus determined is the product of the unit calorific value determined at step 24 X the walking time period X the weight of the subject.

When the fat consumption ratio is stored at step 15 described above, it can be stored together with attendant conditions under which the change in visceral fat has been determined; for example, the kind of exercise such as walking or running, the time zone in which the exercise has been done, and conditions before and after a meal taken after the exercise has been done. It is also possible that the fat consumption ratio is graphically displayed at the display section 7 as a parameter under such attendant conditions.

If the fat consumption ratio is stored at step S15, it is possible in the next-time determination of one of the amounts of a change in visceral fat caused by exercise such as walking, and a consumed calorific value consumed by exercise such as walking that the other is determined from the determined one and the fat consumption ratio stored. Based on fat consumption ratios determined at step S15, it is also possible that the cumulative sum of the fat consumption ratios found by individual determinations is found or that the average of the fat consumption ratios found as a result of a plurality of determinations is found. Since the cumulative sum of such fat consumption ratios reflects the amount of abdominal visceral fat cumulatively consumed over a predetermined period, the cumulative sum can be conveniently utilized in estimating the degree of achievement of an objective which is established as a target consumption of fat over the predetermined period. On the other hand, since the average of fat consumption ratios reflects an average consumption of fat over the predetermined period, the average of fat consumption ratios allows the user easily to appreciate the state of average fat consumption over the predetermined period.

Further, it is possible to find a steps count, walking distance, and consumed calorific value which are required to consume a given amount of abdominal visceral fat as a target (target fat consumption amount) from the fat consumption ratio stored at step S15 and the steps count and consumed calorific value stored at step S10. The visceral fat determining device 10 may be configured to allow such a target fat consumption amount to be established before exercise such as walking and to display an indication that the target fat consumption amount has been reached at the display section 7 or to notify the user of the attainment of the target fat consumption amount by means of an alarm such as a buzzer.

The foregoing description has been directed to a configuration adapted to determine abdominal visceral fat cross-sectional areas before the starting of step counting and after the termination of step counting and then determine a change in abdominal visceral fat caused by exercise such as walking on the basis of the two abdominal visceral fat cross-sectional areas determined before and after exercise such as walking and the step-count data. Consumption of the abdominal visceral fat of a human body starts not just after the starting of exercise, but also after lapse of a certain time period from the starting of consumption of glycogen and the like stored in the human body.

Accordingly, if one wants to know a steps count, or a consumed calorific value or the like corresponding to the amount of abdominal visceral fat directly consumed, it is necessary to know a steps count, a consumed calorific value, or the like, determined after the start of consumption of the abdominal visceral fat itself according to the consumption mechanism of a human body. The relationship between the consumption of abdominal visceral fat itself and such a steps count or consumed calorific value can be determined by the following procedure for example.

The first abdominal visceral fat cross-sectional area is determined before the start of step counting. When the counting of steps involved in exercise such as walking starts, determinations of abdominal visceral fat cross-sectional area are sequentially performed at predetermined time intervals and the results of the determinations are stored together with the corresponding time periods and steps counts. The abdominal visceral fat cross-sectional areas determined at such predetermined time intervals are sequentially compared with the first abdominal visceral fat cross-sectional area until a difference therebetween is detected. Once the difference is detected, the comparison is stopped. The detection of such a difference from the first abdominal visceral fat cross-sectional area by comparison means that consumption of abdominal visceral fat begins. The time period up to the detection of such a difference is a time period from the start of exercise such as walking up to the start of abdominal visceral fat consumption (referred to as "visceral fat combustion starting time period").

A consumed calorific value based on a steps count counted after lapse of such a visceral fat combustion starting time period is directly related to consumption of abdominal visceral fat itself. It is also possible to find a corrected fat consumption ratio relative to the consumption of abdominal visceral fat itself from such a visceral fat combustion starting time period and the second abdominal visceral fat cross-sectional area determined after the termination of the step counting. Such a visceral fat combustion starting time period can be stored with the kind of exercise such as walking or running. In the next-time determination of a fat consumption ratio it is possible to find a corrected fat consumption ratio relative to the consumption of abdominal visceral fat itself with use of an abdominal visceral fat combustion starting time period according to the kind of exercise.

Figure 4:
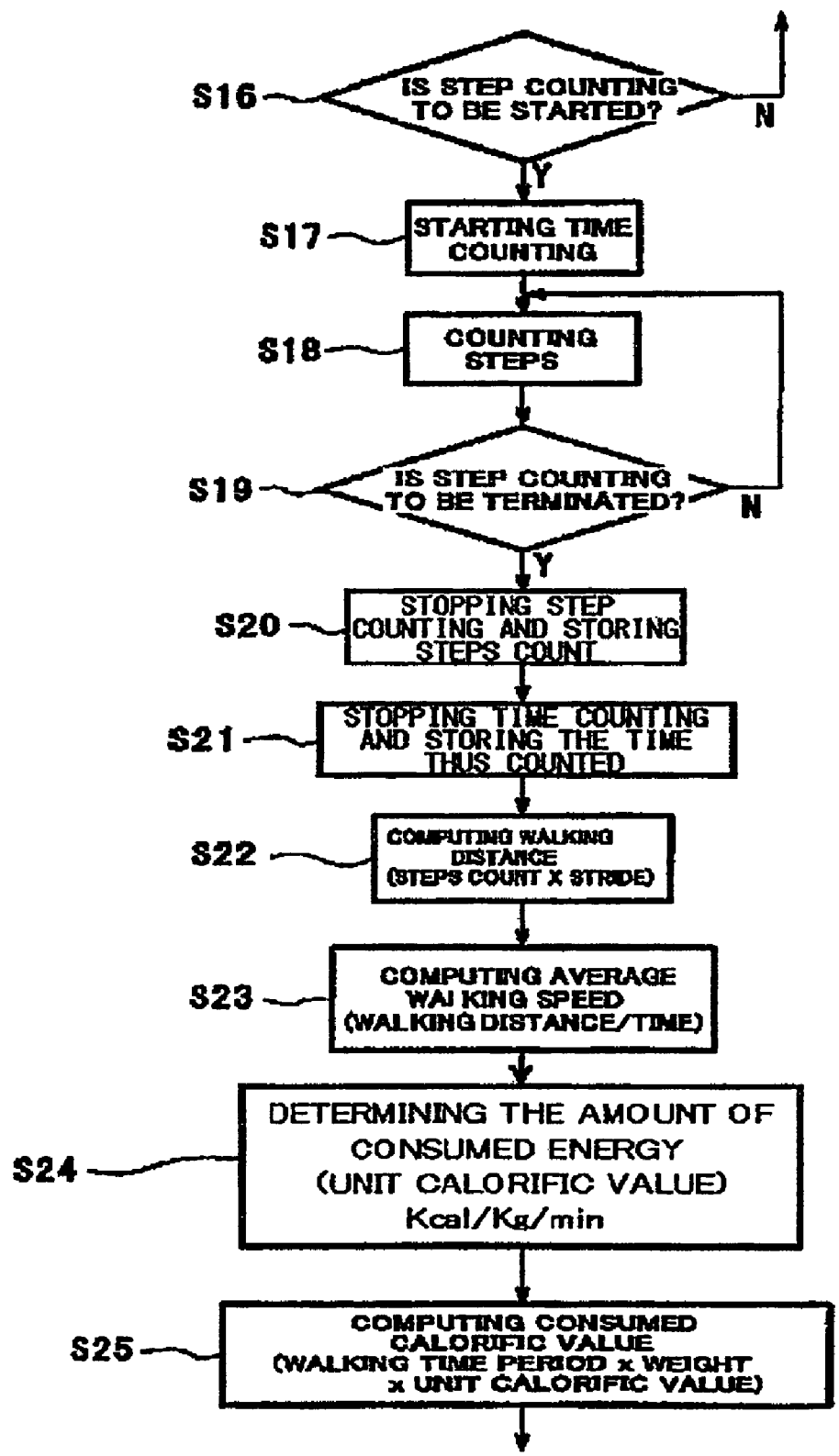
FIG. 4 is a flow chart for determining a consumed calorific value from a walking speed.

In the foregoing description, a consumed calorific value corresponding to an amount of exercise involved in exercise such as walking done by the subject is determined based on values determined in the state of the subject doing exercise such as a steps count involved in such exercise and a walking time period as determined at step S10 in FIG. 3 or at step S25 in FIG. 4.

In relation to the determination of such a consumed calorific value as a result of exercise such as walking, the amount of exercise corresponding to the consumed calorific value can also be determined in the following manner. That is, the subject counts his or her heart rate or pulses after the termination of exercise such as walking through palpation, and a time period up to a predetermined count is measured with the clock 23. The computation processing section 20 performs a computation to find a heart rate or the number of pulses per unit time from the predetermined count of heart rate or the like and the time period measured.

Further, the amount of exercise can be found if the intensity of exercise is determined based on the heat rate or the like per unit time thus found. The determination of an amount of exercise involved in exercise such as walking in this manner allows the degree of intensity of exercise such as walking and the personal characteristics of a subject to be taken into account and hence makes it possible to determine the amount of exercise more accurately.

As described above, the visceral fat determining device with a step-counting function according to the present invention is portable and hence is capable of determining abdominal visceral fat and counting the number of steps involved in exercise such as daily walking. Further, the visceral fat determining device is capable of easily determining a change in visceral fat caused by exercise such as walking and the relationship between the amount of exercise and the amount of the change in abdominal visceral fat.

The visceral fat determining device with a step-counting function described above may be incorporated integrally with various members having portability in addition to the members functioning as a passometer and a visceral fat determining device. For example, the visceral fat determining device may be incorporated with a stopwatch, night lamp, electronic calculator, lighter, mechanical pencil, tie-pin, thermometer, a distance meter for use in golf courses, or the like. The visceral fat determining device thus incorporated with such a member is convenient because the member exercises its function as one of the functions of the visceral fat determining device. It is also possible to incorporate a pulse meter, sphygmomanometer, clinical thermometer, or the like having portability into and integrally with the visceral fat determining device. By so doing, the visceral fat determining device can be used also as a motor ability checker.

The visceral fat determining device 10 described above may be configured to judge whether a subject has the possibility of developing any one of diseases that are likely to be caused by obesity of the subject's body based on body data of the subject inputted or obtained by determinations.

Specifically, criterial reference values including a criterial reference value $J_{BM}$ of BMI, a criterial reference value $J_{WS}$ of waist size, and a criterial reference value $J_{NZ}$ of abdominal visceral fat cross-sectional area are previously stored in the storage section 22. The visceral fat determining device 10 compares the BMI, waist size, and abdominal cross-sectional area of the subject with the criterial reference values $J_{BM}$, $J_{WS}$, and $J_{NZ}$, respectively.

If each of the BMI, waist size, and abdominal visceral fat cross-sectional area of the subject is not less than the corresponding criterial reference value, the subject is judged to have the possibility of developing a disease, whereas if it is less than the corresponding criterial reference value, the subject is judged to have no possibility of developing the disease. The visceral fat determining device 10 may be configured to cause the display section 7 to display each of the judgments, respectively, based on the BMI, waist size, and abdominal visceral fat cross-sectional area of the subject. Alternatively, the visceral fat determining device 10 may be configured to cause the display section 7 to display a symbol "○" representing a judgment on an item having a value less than the corresponding criterial reference value or a symbol "x" representing a judgment on an item having a value not less than the corresponding criterial reference value.

Diseases, the possibility of which can be judged based on the BMI, waist size, and abdominal visceral fat cross-sectional area of a subject, include impaired glucose tolerance such as diabetes, as well as hypertension, lipid metabolic disorder, hyperuricemia, and heart diseases (electrocardiogram disorder).

The visceral fat determining device 10 may be provided with size-measuring means not particularly shown in FIG. 1 for measuring the waist size of a subject. One example of such size-measuring means comprises a measure that is fitted to the visceral fat determining device 10 so as to be accommodated within the visceral fat determining device 10 and allows the subject to know his or her waist size if the measure is drawn out of the visceral fat determining device 10 and trained around a body part to be measured.

The visceral fat determining device 10 thus provided with the size-measuring means is capable of reliably measuring the waist size of the subject in using the visceral fat determining device 10 without the need for separately providing another measure for measuring the waist size and hence is capable of reliably measuring the latest waist size at the time of determination with a high precision.

The visceral fat determining device 10 provided with the size-measuring means may be configured such that, when the measure is being trained around a waist part to be measured to obtain the measurement, data of the waist size thus measured is automatically inputted to the computation processing section 20 and stored in the storage section 22 in response to an operation of the manipulation section 6. Such a configuration allows such a measured waist size to be inputted to the visceral fat determining device 10 without the need of manipulation of the manipulation section 6 by the subject, thereby easing the entry of the waist size.

Though the foregoing description is directed to the embodiment configured to perform a computation to determine the abdominal visceral fat cross-sectional area (VA) of a subject using data including the waist size, BMI, and the like of the subject based on the formulae (1) to (5), the abdominal visceral fat cross-sectional area (VA) can also be determined through a computation using data including the body fat ratio of the subject as one body data item.

The following description is directed to an embodiment configured to be capable of determining the abdominal visceral fat cross-sectional area of a subject on the assumption that the body fat ratio of the subject also correlates with the abdominal visceral fat cross-sectional area. The following formulae (6) to (9) can be stored in the storage section 22 of the visceral fat determining device 10 described above as computing formulae to be used for estimation of the abdominal visceral fat cross-sectional area of a subject through computation.

$$VA = a_3 \cdot W_L + d_1 \cdot \text{FAT} + c_3 \quad (6)$$

$$VA = a_5 \cdot W_L + d_2 \cdot \text{FAT} + e_2 \cdot s + c_5 \quad (7)$$

$$VA = a_6 \cdot W_L + b_3 \cdot \text{BMI} + d_3 \cdot \text{FAT} + c_9 \quad (8)$$

$$VA = a_7 \cdot W_L + b_4 \cdot \text{BMI} + d_4 \cdot \text{FAT} + e_3 \cdot s + c_{10} \quad (9)$$

In the formulae (6) to (9), FAT represents a body fat ratio (%), and $a_3$, $a_5$, $a_6$, $a_7$, $b_3$, $b_4$, $C_3$, $c_5$, $c_9$, $c_{10}$, $d_1$, $d_2$, $d_3$, $d_4$, $e_2$ and $e_3$ are coefficients obtained in the processes of creating these formulae based on statistical processing to be described later.

The formula (6) can be created by assuming that the actual abdominal visceral fat cross-sectional area determined of each individual of the samples has correlations with the waist size ($W_L$) and FAT of that individual and statistically processing the correlations. In the formula (6), the coefficient $a_3$ with respect to $W_L$ is the third regression coefficient of waist size, the coefficient $d_1$ with respect to FAT is the first regression coefficient of body fat ratio, and the coefficient $c_3$ is a third regression coefficient.

The formula (7) can be created by assuming that the actual abdominal visceral fat cross-sectional area determined of each individual of the samples has correlations with the waist size, FAT, and abdominal subcutaneous fat thickness of that individual and statistically processing the correlations. In the formula (7), the coefficient $a_5$ with respect to $W_L$ is the fifth regression coefficient of waist size, the coefficient $d_2$ with respect to FAT is the second regression coefficient of body fat ratio, the coefficient $e_2$ with respect to s is the second regression coefficient of abdominal subcutaneous fat thickness, and the coefficient $c_5$ is a fifth regression coefficient.

The formula (8) can be created by assuming that the actual abdominal visceral fat cross-sectional area determined of each individual of the samples has correlations with the waist size, BMI, and FAT of that individual and statistically processing the correlations. In the formula (8), the coefficient $a_6$ with respect to $W_L$ is the sixth regression coefficient of waist size, the coefficient $b_3$ with respect to BMI is the third regression coefficient of BMI, the coefficient $d_3$ with respect to FAT is the third regression coefficient of body fat ratio, and the coefficient $c_5$ is a ninth regression coefficient.

The formula (9) can be created by assuming that the actual abdominal visceral fat cross-sectional area determined of each individual of the samples has correlations with the waist size, BMI, FAT, and abdominal subcutaneous fat thickness of that individual and statistically processing the correlations. In the formula (9), the coefficient $a_7$ with respect to $W_L$ is the seventh regression coefficient of waist size, the coefficient $b_4$ with respect to BMI is the fourth regression coefficient of BMI, the coefficient $d_4$ with respect to FAT is the fourth regression coefficient of body fat ratio, the coefficient $e_3$ with respect to s is the third regression coefficient of abdominal subcutaneous fat thickness, and the coefficient $c_{10}$ is a tenth regression coefficient.

The determination of the abdominal visceral fat cross-sectional area of a human body serving as a sample in the creation of the formulae (6) to (9) can be achieved by tomography as in the creation of the formulae (1) to (3), and the statistical processing of the correlations between two or more body data items and an abdominal visceral fat cross-sectional area can be achieved by multiple linear regression analysis.

In creating the formulae (6) to (9) the number of human bodies serving as samples for collecting abdominal visceral fat cross-sectional areas and body data is desirably 100 or more, more desirably 500 or more, as in the creation of the formulae (1) to (3).

With the formula (6) described above, it is possible to determine the VA of a subject which reflects the waist size and FAT of the subject because computation is performed using data including the waist size and FAT of the subject as body data of the subject.

With the formula (7) it is possible to determine the VA of a subject which reflects the waist size, FAT, and abdominal subcutaneous fat thickness of the subject because computation is performed using data including the waist size, FAT, and abdominal subcutaneous fat thickness the subject as body data of the subject.

With the formula (8) it is possible to determine the VA of a subject which reflects the waist size, BMI, and FAT of the subject because computation is performed using data including the waist size, BMI, and FAT of the subject as body data of the subject.

With the formula (9) it is possible to determine the VA of a subject which reflects the waist size, BMI, FAT, and abdominal subcutaneous fat thickness of the subject because computation is performed using data including the waist size, BMI, FAT, and abdominal subcutaneous fat thickness the subject as body data of the subject.

Of the formulae (6) to (9) noted above, one for determining the VA of a subject with a larger number of body data items is capable of determining the VA more accurately because it allows the body condition of the subject to be reflected more precisely from additional different angles.

It is possible to add the foregoing correction term of the formula (4) based on the age of a subject or the foregoing correction term of the formula (5) based on the sex of the subject to each of the formulae (6) to (9). If the correction term Yc of the formula (4) or the correction term Xc of the formula (5) is added to each of the formulae (6) to (9) to determine the VA of the subject, the VA thus determined reflects personal characteristics of the subject more precisely based on the age or sex of the subject.

It is possible to add either or both of the correction terms Xc and Yc to each of the formulae (6) to (9). If the correction terms Xc and Yc are both added to each of the formulae (6) to (9) to determine the VA, the VA thus determined reflects personal characteristics of the subject much more precisely.

Body fat ratio (FAT) data used in computations based on the foregoing formulae (6) and (9) may be such data determined by means of a separate body fat determining device or the like and inputted as one body data item to the visceral fat determining device 10 through the manipulation section 6. Alternatively, the visceral fat determining device 10 may be provided with body fat ratio measurement means for obtaining body fat ratio data to be used in the computations based on the formulae (6) to (9).

Such body fat ratio measurement means can be provided in the visceral fat determining device 10 as follows. A pair of electrodes are disposed so that one finger of each of the subject's right and left hands holding the main body 1 of the visceral fat determining device 10 can contact the pair of electrodes, while another pair of electrodes disposed so that another finger of each of the subject's right and left hands can contact the aforesaid another pair of electrodes.

The former pair of electrodes are used as a pair of current path forming electrodes through which a current path is formed between both hands as terminals of a human body, while the aforesaid another pair of electrodes used as a pair of voltage-measuring electrodes through which a potential difference between the both hands is measured.

The pair of current path-forming electrodes are electrically connected to a current source to form a current path in the human body, while the pair of voltage-measuring electrodes electrically connected to voltage-measuring means to measure the voltage across the voltage-measuring electrodes, thereby measuring the impedance between the both hands of the subject.

In determining the body fat ratio of a subject body data such as the weight, height, sex, and age of the subject, as well as the impedance of the subject, is necessary. For this reason, the visceral fat determining device 10 has to be configured to allow entry of all the necessary body data items through the manipulation section 6 without lack.

Further, a predetermined computing formula for finding a body fat ratio from such an impedance and body data through a computation is stored in the storage section 22 to allow the computation section 20 to perform the computation to find the body fat ratio.

An embodiment of the visceral fat determining device with a step-counting function according to the present invention may be configured to be capable of determining the abdominal visceral fat cross-sectional area (VA) of a human body through a computation using data including an item related to the impedance of the human body.

The following description is directed to such an embodiment configured to be capable of determining the abdominal visceral fat cross-sectional area of a subject on the assumption that the impedance of the body of the subject also correlates with the abdominal visceral fat cross-sectional area. The following formula (10) is stored in the storage section 22 of the visceral fat determining device 10 described above as a computing formula for a computation to estimate the abdominal visceral fat cross-sectional area (VA) to be stored in the storage section 22.

$$VA = a_8 \cdot W_L + g_1 \cdot (T_L^2/Z) + c_{11} \quad (10)$$

In the formula (10), Z represents the impedance of a human body, $T_L$ represents the height of the subject, and $a_8$, $g_1$, and $c_{11}$ are coefficients obtained in the process of creating this formula based on statistical processing to be described later.

With the formula (10) it is possible to determine the abdominal visceral fat cross-sectional area (VA) of a subject from the waist size of the subject and the term $((T_L)^2/Z)$ which is obtained by dividing the square of the value of the height of the subject by the impedance of the body of the subject. In the formula (10), $((T_L)^2/Z)$ is the data item related to the impedance of a human body.

The formula (10) can be created by assuming that the actual abdominal visceral fat cross-sectional area determined of each individual of the samples has correlations with the waist size and $((T_L)^2/Z)$ of that individual and statistically processing the correlations. In the formula (10), the coefficient $a_8$ with respect to $W_L$ is the eighth regression coefficient of waist size, the coefficient $g_1$ with respect to $((T_L)^2/Z)$ is the first regression coefficient of $((T_L)^2/Z)$, and the coefficient $c_{11}$ is an eleventh regression coefficient.

The determination of the abdominal visceral fat cross-sectional area of a human body serving as a sample in the creation of the formula (10) can also be achieved by tomography as in the creation of the formulae (1) to (3), and the statistical processing of the correlations between two or more body data items and an abdominal visceral fat cross-sectional area can be achieved by multiple linear regression analysis.

In creating the formula (10) the number of human bodies serving as samples for collecting abdominal visceral fat cross-sectional areas and body data is desirably 100 or more, more desirably 500 or more, as in the creation of the formulae (1) to (3).

With the formula (10) described above, it is possible to determine the VA of a subject which reflects the waist size and $((T_L)^2/Z)$ of the subject because computation is performed using data including the waist size and $((T_L)^2/Z)$ of the subject as body data of the subject.

It is possible to add the foregoing correction term of the formula (4) based on the age of a subject or the foregoing correction term of the formula (5) based on the sex of the subject to the formula (10) to the formula (10). If the correction term Yc of the formula (4) or the correction term Xc of the formula (5) is added to the formula (10) to determine the VA of the subject, the VA thus determined reflects personal characteristics of the subject more precisely based on the age or sex of the subject.

It is possible to add either or both of the correction terms Xc and Yc to the formula (10). If the correction terms Xc and Yc are both added to the formula (10) to determine the VA, the VA thus determined reflects personal characteristics of the subject much more precisely.

Impedance data used in the computation based on the foregoing formula (10) may be such data determined by means of a separate device or the like and inputted as one body data item to the visceral fat determining device 10 through the manipulation section 6.

Alternatively, the visceral fat determining device 10 may be provided with body fat ratio measurement means and configured to allow the data of an impedance measured by impedance measurement means 12 included in the body fat ratio measurement means to be inputted to the computation processing section 20 and used in the computation.

The following formula (11) can be created as a computing formula for determining the abdominal visceral fat cross-sectional area (VA) of a subject if an impedance (Z) is used as the body data item related to impedance.

$$VA = a_9 \cdot W_L + g_2 \cdot Z + c_{12} \quad (11)$$

In the formula (11), $a_9$, $g_2$ and $c_{12}$ are coefficients obtained in the process of creating this formula (11) based on statistical processing.

As described regarding the formula (10), the formula (11) can be created by assuming that the actual abdominal visceral fat cross-sectional area determined of each individual of the samples has correlations with the waist size and impedance (Z) of that individual and statistically processing the correlations. In the formula (11), the coefficient $a_2$ with respect to $W_L$ is the ninth regression coefficient of waist size, the coefficient $g_2$ with respect to (Z) is the second regression coefficient of impedance (Z), and the coefficient $c_{12}$ is a twelfth regression coefficient.

The determination of the abdominal visceral fat cross-sectional area of a human body serving as a sample in the creation of the formula (11) can be achieved by tomography as in the creation of the foregoing formulae, and the statistical processing of the correlations between two or more body data items and an abdominal visceral fat cross-sectional area can be achieved by multiple linear regression analysis. The number of human bodies serving as samples is desirably 100 or more, more desirably 500 or more.

With the formula (11) it is possible to determine the VA of a subject which reflects the waist size and impedance of the subject because the computation for determining the VA is performed using data including the waist size and impedance of the subject as body data of the subject. The entry of the data of an impedance to be used in the computation based on the formula (11) can be achieved in the same manner as with the formula (10); that is, the data of an impedance may be inputted through the manipulation section 6, or the visceral fat determining device 10 is provided with body fat ratio measurement means and the data of an impedance measured by impedance measurement means 12 included in the body fat ratio measurement means is inputted to the computation processing section 20 and used in the computation.

It is possible to add the foregoing correction term of the formula (4) or the correction term of the formula (5) to the formula (11). If so, the VA determined reflects personal characteristics of the subject more precisely based on the age or sex of the subject. It is possible to add either or both of the correction terms Xc and Yc to the formula (11). If the correction terms Xc and Yc are both added to the formula (11), the VA determined reflects personal characteristics of the subject much more precisely.

Further, the visceral fat determining device with a step-counting function according to the present invention may be configured to be capable of determining the abdominal visceral fat cross-sectional area (VA) of a human body based on the assumption that $(W_L^2 \cdot T_L \cdot age)$ and $(W_L^2 \cdot T_L \cdot FAT)$ have correlation with each other. The following formula (12) is stored in the storage section 22 of the visceral fat determining device 10 described above as a computing formula for estimating the abdominal visceral fat cross-sectional area (VA) of a subject through a computation.

$$VA = i_1 \cdot W_L^2 \cdot T_L \cdot age + h_1 \cdot W_L^2 \cdot T_L \cdot FAT - c_{13} \quad (12)$$

In the formula (12), $W_L$ represents the waist size of the subject, $T_L$ represents the height of the subject, age represents the age of the subject, and FAT represents the body fat ratio of the subject. Further, in the formula (12), $i_1$, $h_1$, and $c_{13}$ are coefficients obtained in the process of creating this formula based on statistical processing to be described later.

The formula (12) can be created by assuming that the actual abdominal visceral fat cross-sectional area determined of each individual of the samples has correlations with $(W_L^2 \cdot T_L \cdot age)$ and $(W_L^2 \cdot T_L \cdot FAT)$ of that individual and statistically processing the correlations. In the formula (12), the coefficient $i_1$ with respect to $(W_L^2 \cdot T_L \cdot age)$ is the first regression coefficient of $(W_L^2 \cdot T_L \cdot age)$, the coefficient $h_1$ with respect to $(W_L^2 \cdot T_L \cdot FAT)$ is the first regression coefficient of $(W_L^2 \cdot T_L \cdot FAT)$, and the coefficient $c_{13}$ is a thirteenth regression coefficient.

With the formula (12), it is possible to obtain an estimated value of VA accurately if the subject is a man. Accordingly, in the case where the sex of the subject inputted through the manipulation section 7 is male, selection of the formula (12) makes it possible to find an estimated value of VA of a male subject accurately With the formula (12) it is also possible to determine the VA of the subject which reflects $(W_L^2 \cdot T_L \cdot age)$ and $(W_L^2 \cdot T_L \cdot FAT)$ of the subject because the computation is performed using data including $(W_L^2 \cdot T_L \cdot age)$ and $(W_L^2 \cdot T_L \cdot FAT)$ of the subject as body data of the subject.

Alternatively, the visceral fat determining device with a step-counting function according to the present invention may be configured to be capable of determining the abdominal visceral fat cross-sectional area (VA) of a human body based on the assumption that $(W_L^2 \cdot T_L \cdot age)$ and the body fat ratio FAT of the subject have correlation with each other. The following formula (13) is stored in the storage section 22 of the visceral fat determining device 10 described above as a computing formula for estimating the abdominal visceral fat cross-sectional area (VA) of a subject through a computation.

$$VA = i_2 \cdot W_L^2 \cdot T_L \cdot age + d_5 \cdot FAT - c_{14} \quad (13)$$

In the formula (13), $W_L$ represents the waist size of a subject, $T_L$ represents the height of the subject, age represents the age of the subject, and FAT represents the body fat ratio of the subject. Further, in the formula (13), $i_2$, $d_5$ and $c_{14}$ are coefficients obtained in the process of creating this formula based on statistical processing to be described later.

The formula (13) can be created by assuming that the actual abdominal visceral fat cross-sectional area determined of each individual of the samples has correlations with $(W_L^2 \cdot T_L \cdot age)$ and FAT of that individual and statistically processing the correlations. In the formula (13), the coefficient $i_2$ with respect to $(W_L^2 \cdot T_L \cdot age)$ is the second regression coefficient of $(W_L^2 \cdot T_L \cdot age)$, the coefficient $d_5$ with respect to FAT is the fifth regression coefficient of body fat ratio FAT, and the coefficient $c_{14}$ is a fourteenth regression coefficient.

With the formula (13), it is possible to obtain an estimated value of VA accurately if the subject is a woman. Accordingly, in the case where the sex of the subject inputted through the manipulation section 7 is female, selection of the formula (13) makes it possible to find an estimated value of VA of a female subject accurately.

With the formula (13), it is also possible to determine the VA of the subject which reflects $(W_L^2 \cdot T_L \cdot age)$ and FAT of the subject because the computation is performed using data including $(W_L^2 \cdot T_L \cdot age)$ and FAT of the subject as body data of the subject.

The determination of the abdominal visceral fat cross-sectional area of a human body serving as a sample in the creation of the formulae (12) and (13) can be achieved by tomography as in the foregoing formula, and the statistical processing of the correlations between two or more body data items and an abdominal visceral fat cross-sectional area can be achieved by multiple linear regression analysis. The number of human bodies serving as samples is desirably 100 or more, more desirably 500 or more.

The data of a body fat ratio (FAT) to be used in the computation based on the formula (12) or (13) may be such data determined by means of a separate body fat determining device or the like and inputted as one body data item to the visceral fat determining device 10 through the manipulation section 6. Alternatively, the visceral fat determining device 10 may be provided with body fat ratio measurement means and configured to use the data of a body fat ratio measured by the body fat ratio measurement means.

It is possible to add the foregoing correction term of the formula (4) or the correction term of the formula (5) to each of the formulae (12) and (13). If the correction term is added, the VA determined by the formula (12) or (13) reflects personal characteristics of the subject more precisely based on the age or sex of the subject. It is possible to add either or both of the correction terms Xc and Yc to each of the formulae (12) and (13). If the correction terms Xc and Yc are both added to each of the formulae (12) and (13), the VA determined by the formula (12) or (13) reflects personal characteristics of the subject much more precisely.

INDUSTRIAL APPLICABILITY

The visceral fat determining device with a step-counting function according to the present invention is portable and capable of realizing determinations in relation to abdominal visceral fat and counting the number of steps involved in exercise such as walking readily in everyday life. Further, the visceral fat determiing device allows the user to know the relationship between an amount of exercise involved in exercise such as walking or a consumed calorific value and abdominal visceral fat consumed by such exercise.

The invention claimed is:

1. A visceral fat determining device with a step-counting function, comprising:
   a main body shaped to be portable,
   step-counting means for counting the number of steps involved in exercise such as walking done by a subject,
   data input means for allowing entry of body data of The subject including the waist size of the subject, which is the circumferential size of a trunk part of the subject,
   computing means for obtaining quantitative information about abdominal visceral fat of the subject through a computation of the body data based on a predetermined computing formula,
   storage means for storing a criterial reference value $J_{ws}$ of the waist size, and
   display means for displaying results of determinations obtained, wherein the computing means obtains the quantitative information about abdominal visceral fat of the subject based on the computing formula using data including the waist size of the subject, and compares the waist size with the criterial reference value Jws of the waist size and determines whether a subject has the possibility of developing any one of the diseases that are likely to be caused by obesity of the subject's body based on the comparison, the display means is capable of displaying at least The number of steps counted by the step-counting means and the result of the determination, the quantitative information about abdominal visceral fat is the abdominal visceral fat cross-sectional area of the subject, the storage means further stores a criterial reference value $J_{NZ}$ of abdominal visceral fat cross-sectional area, the computing means further compares the abdominal visceral fat cross-sectional area with the criterial reference value $J_{NZ}$ of abdominal visceral fat cross-sectional ares and determines whether a subject has the possibility of developing any one of diseases that are likely to be caused by obesity of the subject's body based on the comparisons; and wherein the visceral fat determining device with a step-counting function has impedance measurement means capable of measuring the impedance of the body of the subject via electrodes brought into contact with terminals of the body of the subject, the computing formula for determining the abdominal visceral fat cross-sectional area of the subject is created by statistical processing of correlations between actual visceral fat cross-sectional areas of a large number of human bodies as samples that are measured by tomography of the abdominal parts of the human bodies and body data of the human bodies as the samples; and the computation based on the computing formula for determining the abdominal visceral fat cross-sectional area is performed using data including the waist size of the subject and the impedance of the body of the subject, the computing formula being $$VA = A_g \cdot W + g_2 \cdot Z + c_{12}$$

wherein Z is the impedance of a human body, and $a_g$, $g_2$ and $c_{12}$ are regression coefficients.

2. The visceral fat determining device with a step-counting function according to claim 1, wherein:

the step-count data obtained by the step-counting means is stored, and the visceral fat determining device further comprising visceral fat change computing means for performing a computation to find a change in abdominal visceral fat cross-sectional area relative to the step-count data based on a first abdominal visceral fat cross-sectional area determined through a computation based on first body data, step-count data counted by the step-counting means after the first abdominal visceral fat cross-sectional ama is determined, and a second abdominal visceral fat cross-sectional area determined thereafter through a computation based on second body data.

* * * * *